(12) United States Patent
Bressler et al.

(10) Patent No.: US 7,736,384 B2
(45) Date of Patent: *Jun. 15, 2010

(54) CARTRIDGE FOR VASCULAR DEVICE

(75) Inventors: James Erich Bressler, Langhorne, PA (US); Richard T. Briganti, Schwenksville, PA (US); John H. Thinnes, Jr., Philadelphia, PA (US); James F. McGuckin, Jr., Radnor, PA (US)

(73) Assignee: Rex Medical, L.P., Conshohocken, PA (US)

( * ) Notice: Subject to any disclaimer, the term of this patent is extended or adjusted under 35 U.S.C. 154(b) by 1020 days.

This patent is subject to a terminal disclaimer.

(21) Appl. No.: 11/030,929

(22) Filed: Jan. 7, 2005

(65) Prior Publication Data

US 2006/0155321 A1  Jul. 13, 2006

(51) Int. Cl.
*A61F 2/06* (2006.01)
(52) U.S. Cl. ........................ 623/1.11; 606/200
(58) Field of Classification Search ........... 606/200, 606/159, 108; 604/218, 220, 221, 240, 242, 604/243, 533–535, 241, 57, 59, 60, 64, 164.01; 623/1.11, 2.11
See application file for complete search history.

(56) References Cited

U.S. PATENT DOCUMENTS

| | | | |
|---|---|---|---|
| 2,453,901 A * | 11/1948 | Gonsett et al. ................ 7/138 |
| 3,744,492 A | 7/1973 | Leibinsohn | |
| 4,266,815 A * | 5/1981 | Cross .......................... 285/330 |
| 4,425,908 A | 1/1984 | Simon | |
| 5,067,957 A | 11/1991 | Jervis | |
| 5,152,777 A | 10/1992 | Goldberg et al. | |
| 5,188,616 A * | 2/1993 | Nadal .......................... 604/218 |
| 5,324,304 A | 6/1994 | Rasmussen | |
| 5,479,938 A | 1/1996 | Weier | |
| 5,626,605 A | 5/1997 | Irie et al. | |
| 5,681,347 A | 10/1997 | Cathcart et al. | |
| 5,755,790 A | 5/1998 | Chevillon et al. | |
| 5,836,968 A | 11/1998 | Simon et al. | |
| 5,895,410 A | 4/1999 | Fober et al. | |
| 6,099,549 A | 8/2000 | Bosma et al. | |
| 6,165,179 A | 12/2000 | Cathcart et al. | |
| 6,165,198 A | 12/2000 | McGurk et al. | |
| 6,168,603 B1 | 1/2001 | Leslie et al. | |
| 6,231,589 B1 | 5/2001 | Wessman et al. | |
| 6,328,755 B1 | 12/2001 | Marshall | |
| 6,331,176 B1 * | 12/2001 | Becker et al. ................ 604/533 |

(Continued)

OTHER PUBLICATIONS

Instructions for Use, Cordis OPTEASE Permanent Vena Cava Filter,—Cordis Johnson & Johnson Company.

(Continued)

*Primary Examiner*—(Jackie) Tan-Uyen T Ho
*Assistant Examiner*—Dianne Dornbusch
(74) *Attorney, Agent, or Firm*—Neil D. Gershon

(57) ABSTRACT

A cartridge for holding a vascular device and connectable to a component of a delivery system comprising a housing having a first end and a second end, and an engagement member movable to a first engageable position to engage the component of a delivery system to connect the cartridge to the component in a first orientation. A control member is preferably operatively associated with the engagement member to move the engagement member to the first engageable position.

12 Claims, 11 Drawing Sheets

U.S. PATENT DOCUMENTS

| | | |
|---|---|---|
| 6,331,184 B1 | 12/2001 | Abrams |
| 6,342,062 B1 | 1/2002 | Suon et al. |
| 6,447,530 B1 | 9/2002 | Ostrovsky et al. |
| 6,537,294 B1 | 3/2003 | Boyle et al. |
| 6,544,280 B1 | 4/2003 | Daniel et al. |
| 6,569,183 B1 | 5/2003 | Kim et al. |
| 6,623,506 B2 | 9/2003 | McGuckin, Jr. et al. |
| 6,706,053 B1 | 3/2004 | Boylan et al. |
| 6,712,835 B2 | 3/2004 | Mazzocchi et al. |
| 6,726,621 B2 | 4/2004 | Suon et al. |
| 6,783,538 B2 | 8/2004 | McGuckin, Jr. et al. |
| 6,793,665 B2 | 9/2004 | McGuckin, Jr. et al. |
| 6,814,746 B2 | 11/2004 | Thompson |
| 6,989,021 B2 * | 1/2006 | Bosma et al. ............... 606/200 |
| 6,994,092 B2 | 2/2006 | Van de Burg et al. |
| 7,037,321 B2 | 5/2006 | Sachdeva et al. |
| 7,097,651 B2 | 8/2006 | Harrison et al. |
| 7,316,708 B2 | 1/2008 | Gordon |
| 7,338,512 B2 | 3/2008 | McGuckin et al. |
| 2003/0195555 A1 | 10/2003 | Khairkhhan et al. |
| 2005/0004596 A1 | 1/2005 | McGuckin et al. |
| 2005/0015111 A1 | 1/2005 | McGuckin et al. |
| 2005/0165442 A1 | 7/2005 | Thinnes, Jr. et al. |
| 2005/0209631 A1 * | 9/2005 | Galdonik et al. ............ 606/200 |

OTHER PUBLICATIONS

Instructions for Use, Recovery Filter System for Use in Vena Cava—C. R.Bard 2003.

Vena Tech LP Vena Cava Filter, B. Braun Medical Inc., 2001.

Vena Tech LP, Femoral Approach, B. Braun Medical Inc., 2001.

Cordis Endovascular, Instruction for Use, Cordis TRAPEASE™ Permanent Vena Cava Filter and Introduction Kit, Jun. 2001.

LGM (Vena Tech) Vena Cava Filter: Clinical Experience in 64 Patients, Millward, et al, JVIR vol. 2, No. 4, Nov. 1991, pp. 429-433.

Caval Interruption Methods; Comparison of Options, by Thomas A. Whitehill, Seminars in Vascular Surgery, vol. 9, No. 1 (Mar. 1996), pp. 59-69.

* cited by examiner

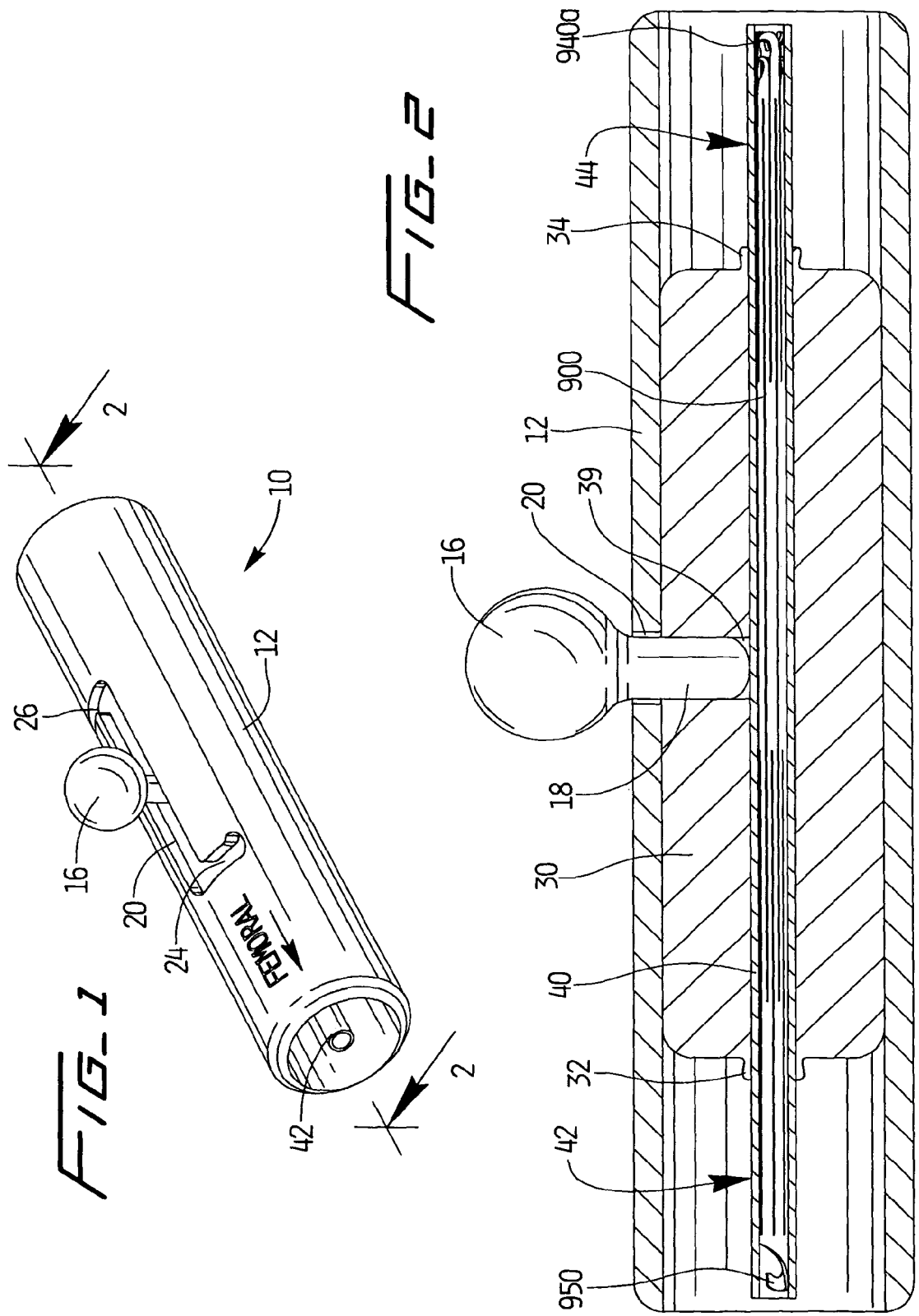

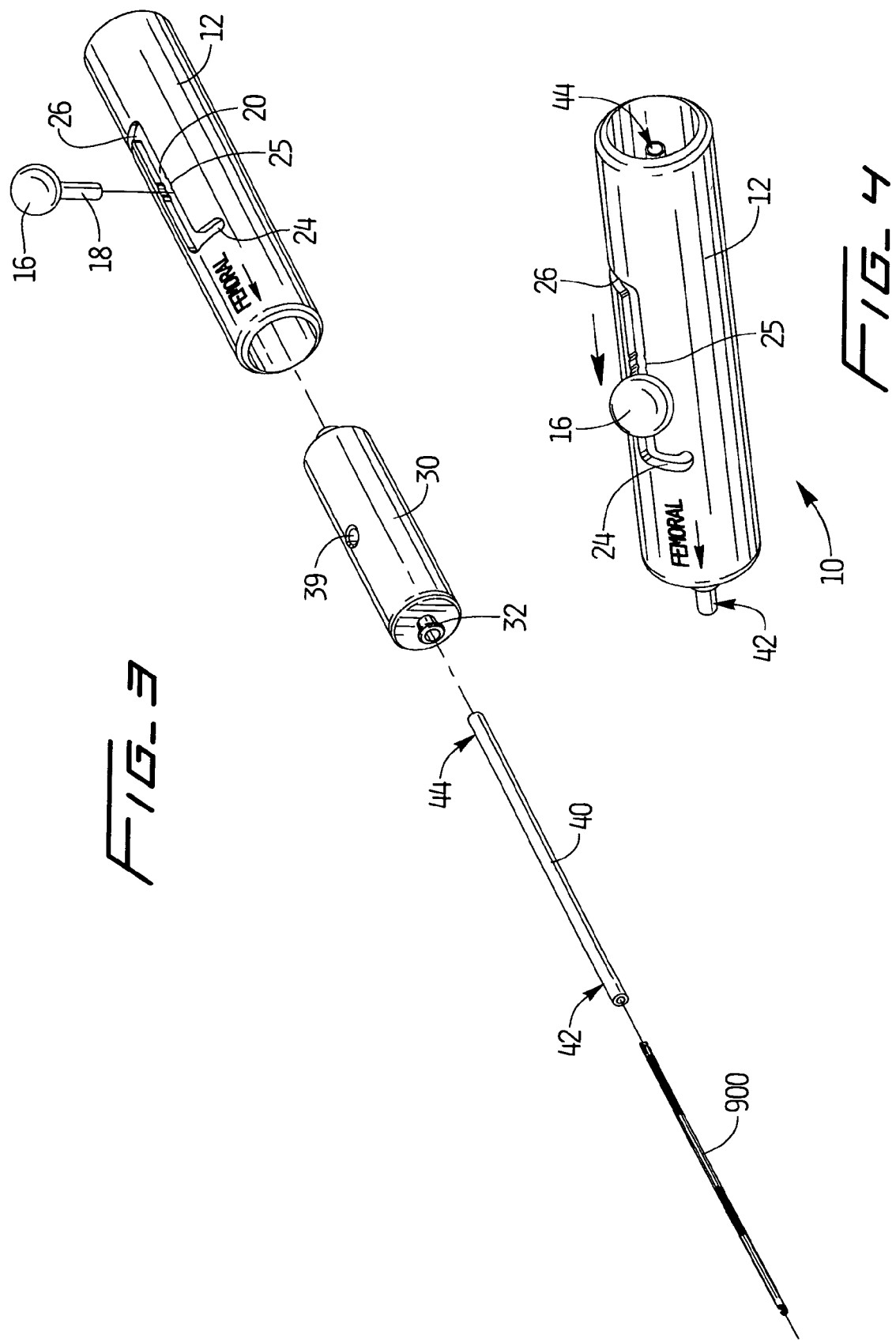

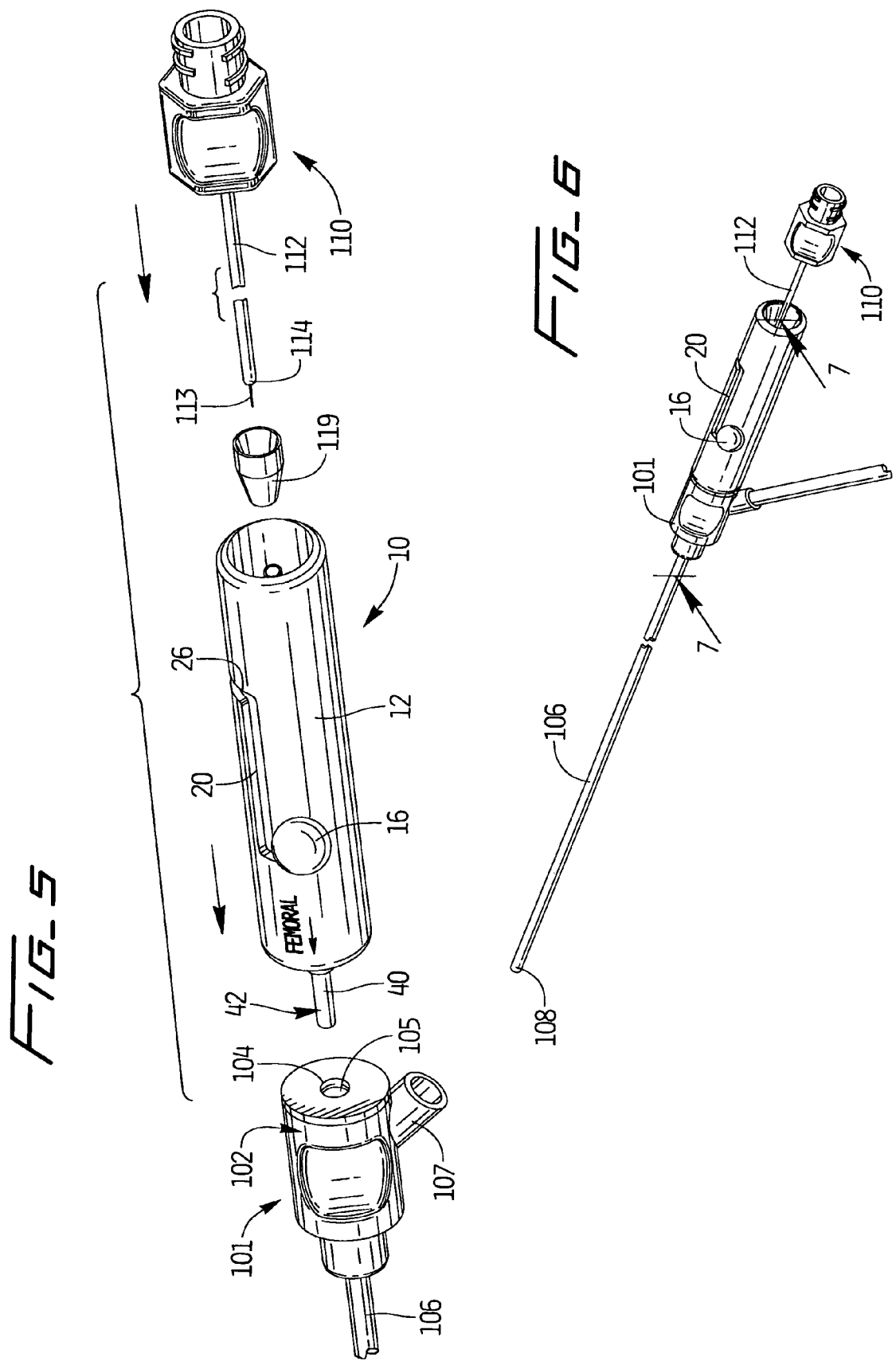

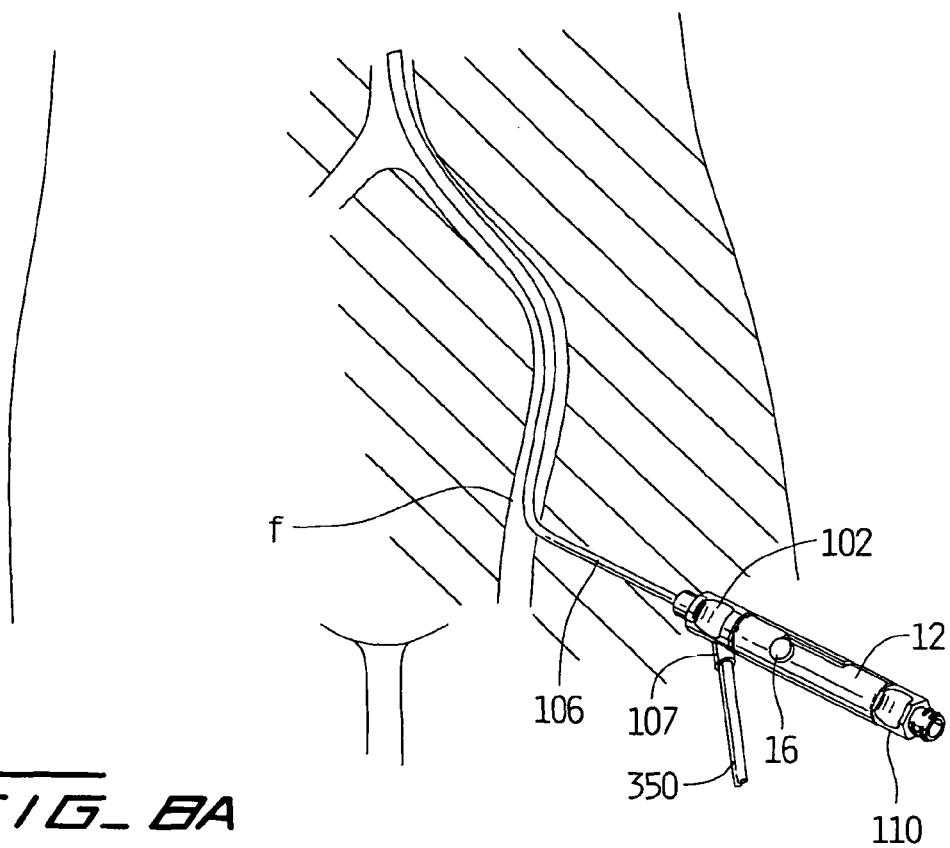
FIG_8A
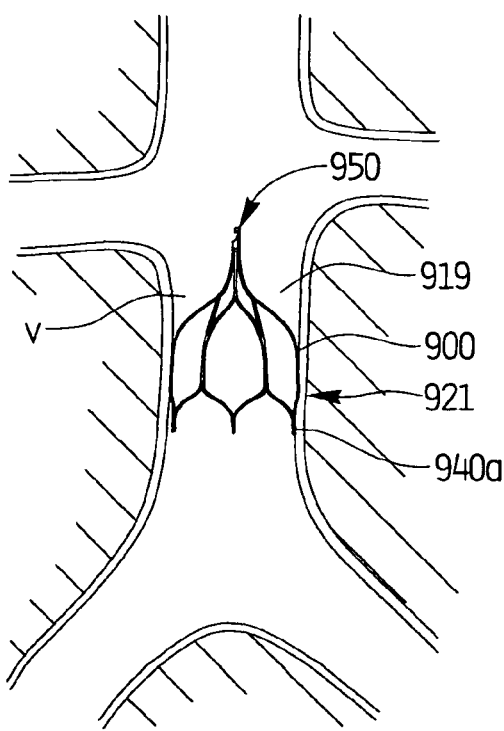
FIG_8B

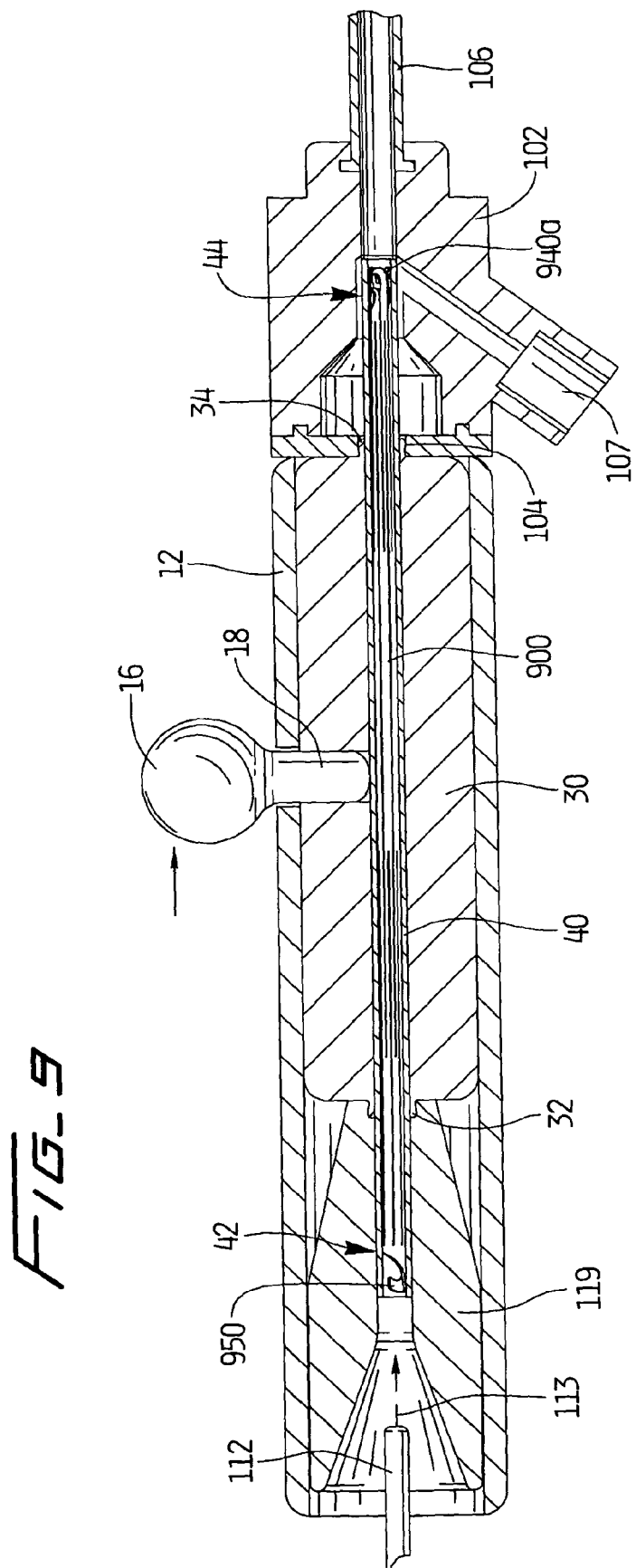

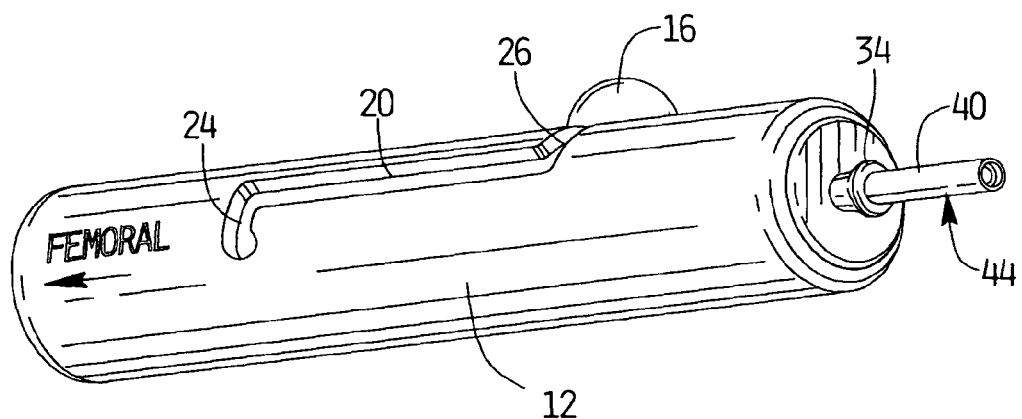
FIG_10
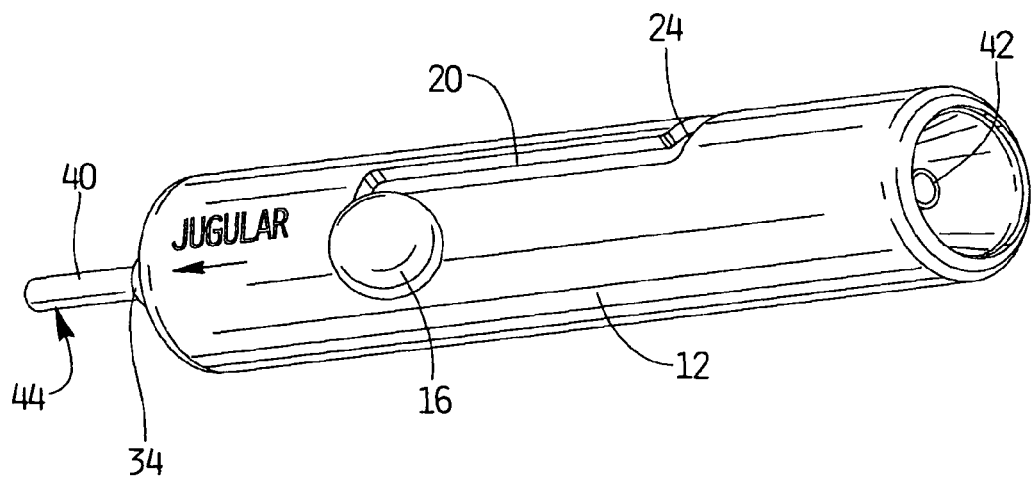
FIG_10A

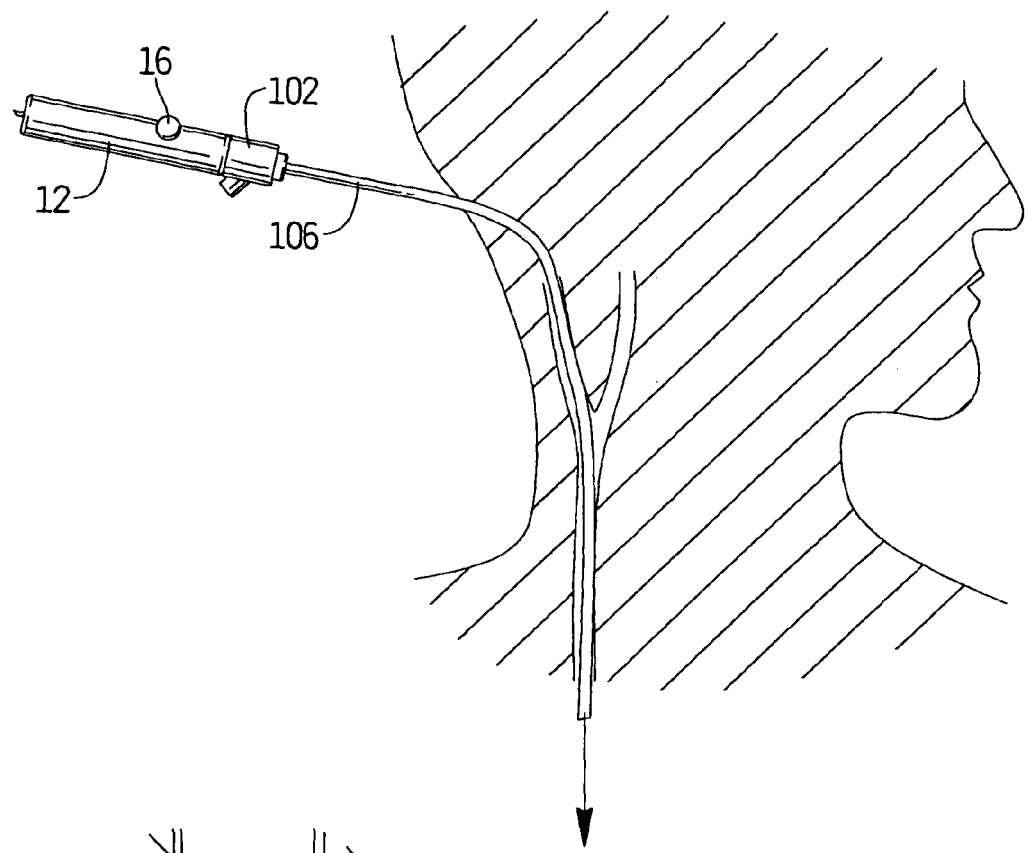
FIG_11A
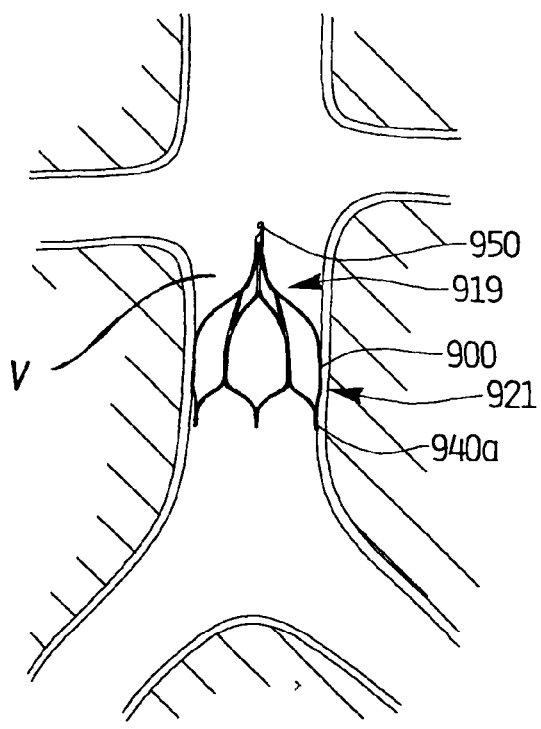
FIG_11B

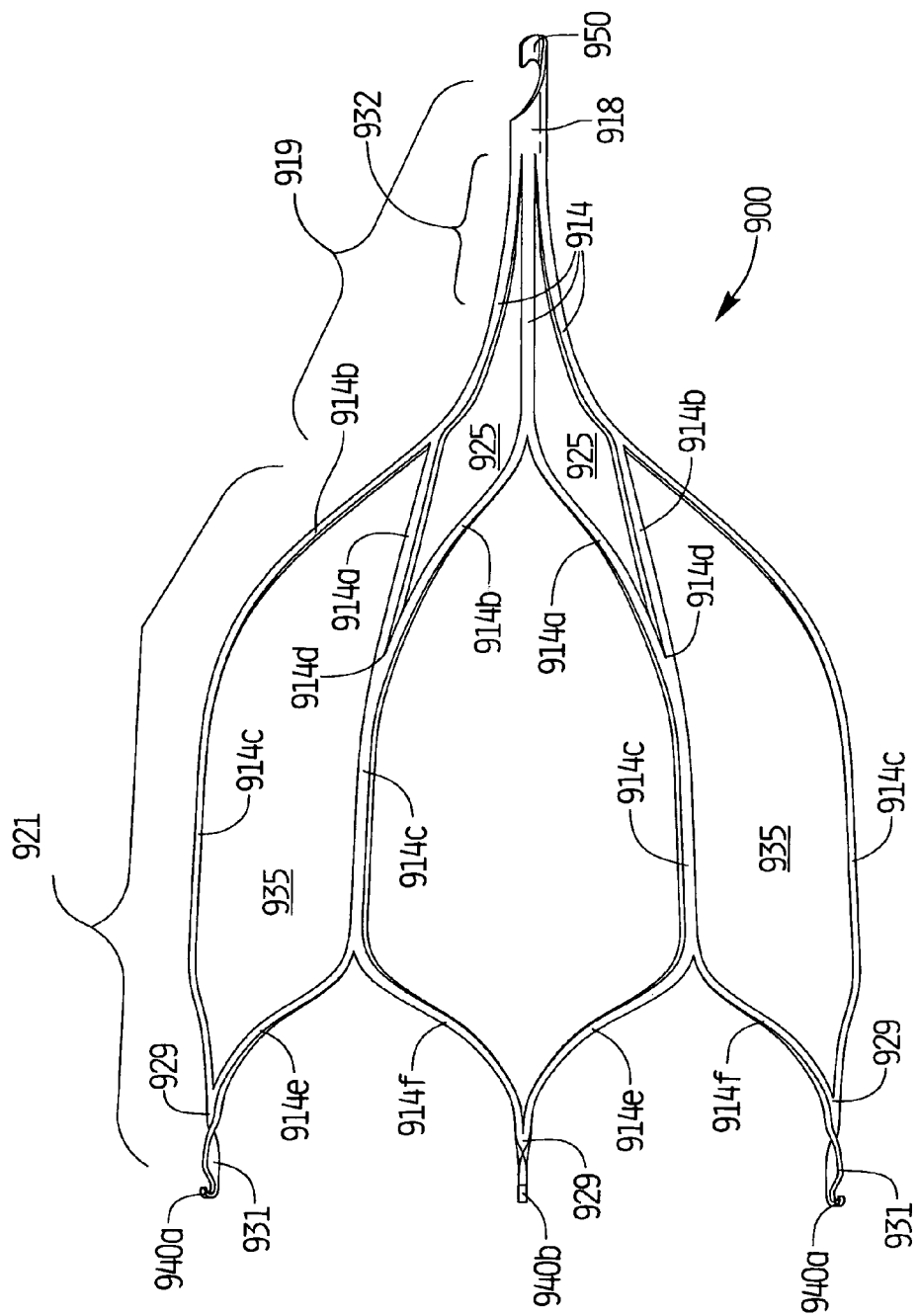

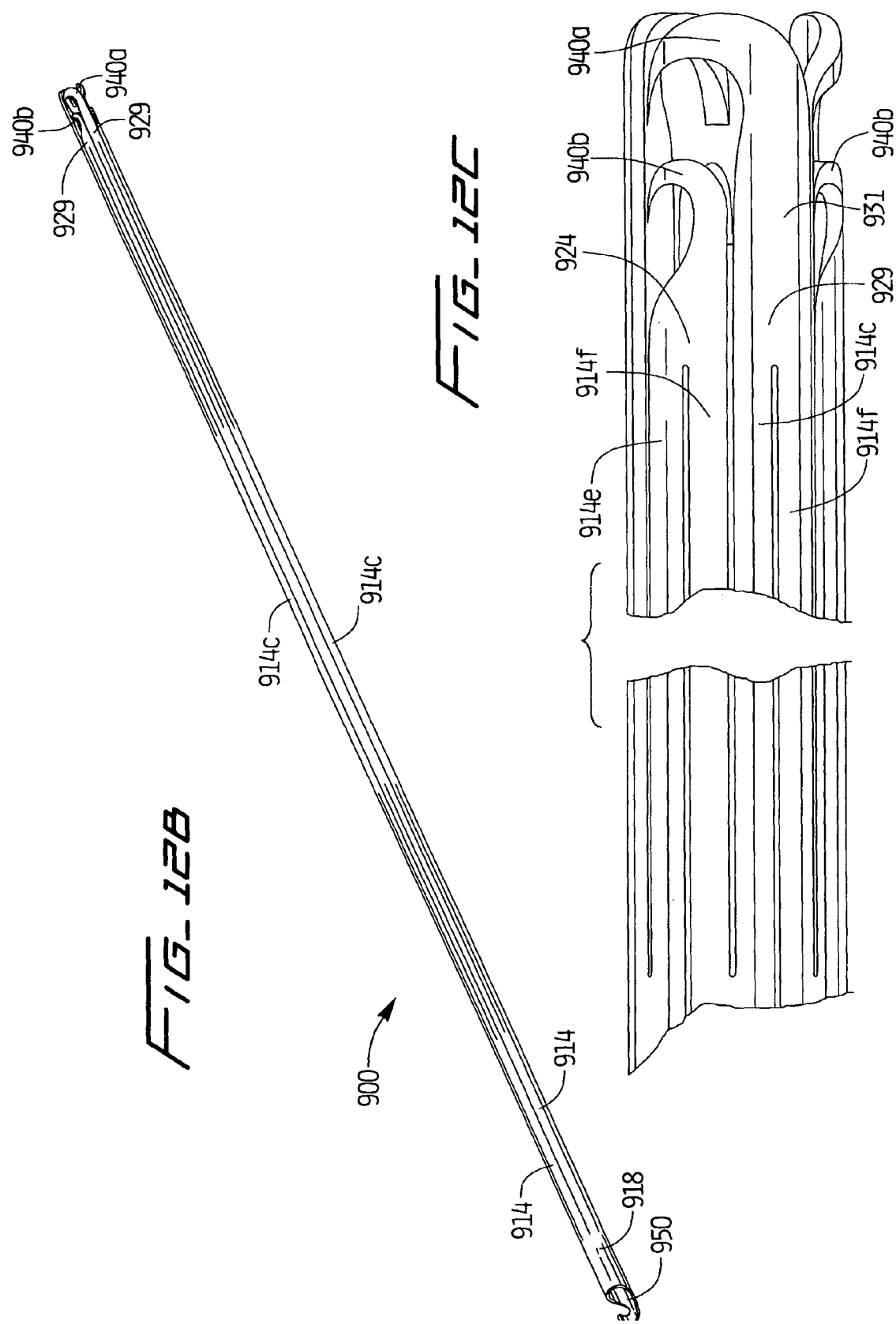

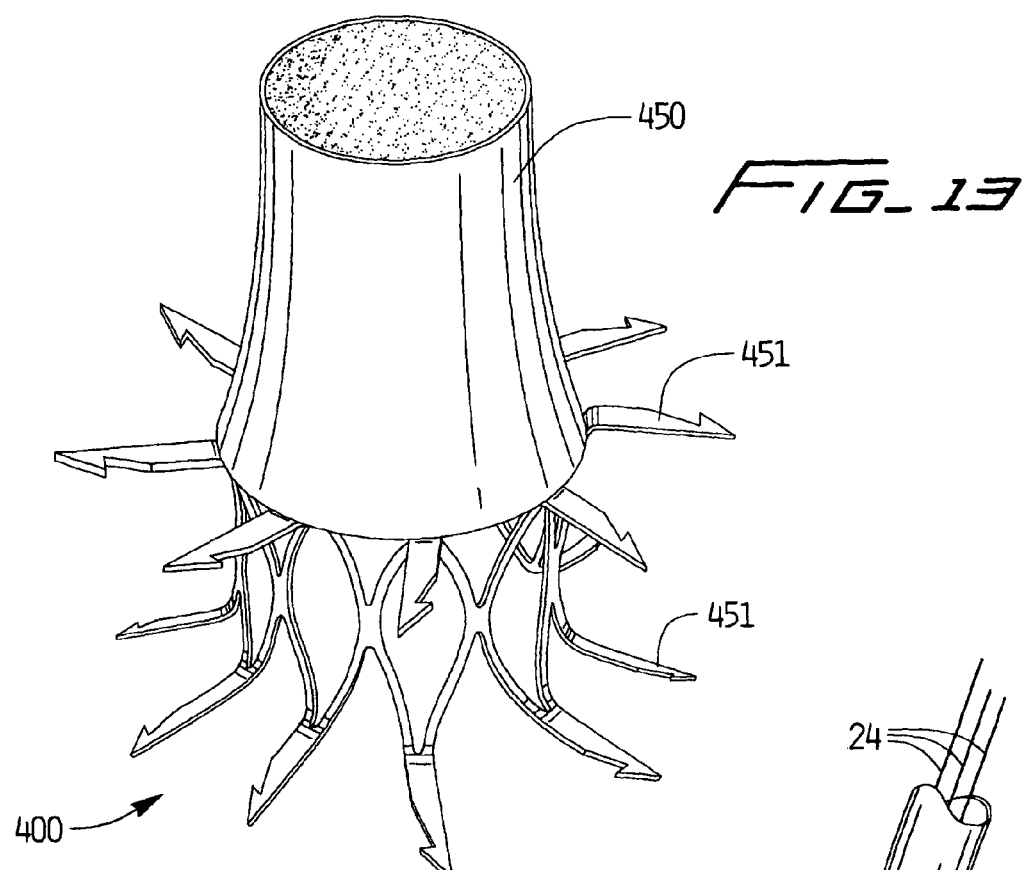
FIG_13
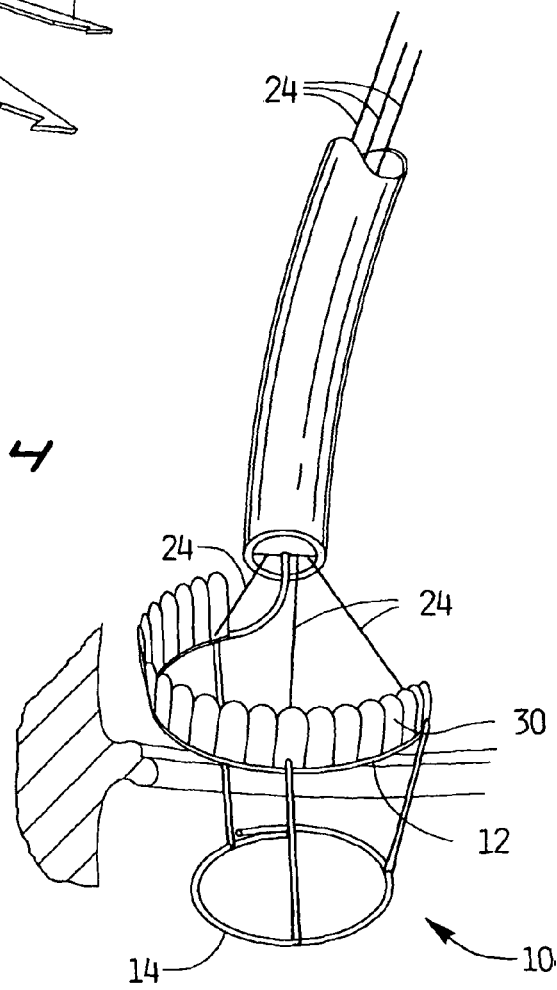
FIG_14

CARTRIDGE FOR VASCULAR DEVICE

BACKGROUND

1. Technical Field

This application relates to delivery of a vascular device and more particularly to a cartridge containing a vascular device such as a vein filter for mounting to a component of a delivery system.

2. Background of Related Art

Passage of blood clots to the lungs is known as pulmonary embolism. These clots typically originate in the veins of the lower limbs and can migrate through the vascular system to the lungs where they can obstruct blood flow and therefore interfere with oxygenation of the blood. Pulmonary embolisms can also cause shock and even death.

In some instances, blood thinning medication, e.g. anticoagulants such as Heparin, or sodium warfarin can be given to the patient. These medications, however, have limited use since they may not be able to be administered to patients after surgery or stroke or given to patients with high risk of internal bleeding. Also, this medication approach is not always effective in preventing recurring blood clots.

Therefore, surgical methods to reduce the likelihood of such pulmonary embolisms by actually blocking the blood clot from reaching the lungs have been developed. One surgical method of treatment involved major surgery where the size of the vessel lumen was restricted by placement of ligatures or clips around the vein, e.g. the inferior vena cava which transports blood from the lower portion of the body to the heart and lungs. This prevented passage of dangerously large blood clots through the vein to the lungs. However, this approach is an invasive surgical procedure, requiring an abdominal incision and general anesthesia and frequently causing vessel thrombosis and lower extremity swelling. Also, there is a lengthy patient recovery time and additional hospital and surgeon expenses associated with this major surgery. In fact, oftentimes, the patients requiring the surgery are unhealthy and the major surgery and general anesthesia poses a risk in and of itself.

To avoid such invasive surgery, less invasive surgical techniques have been developed. These involve the placement of a mechanical barrier in the inferior vena cava. These barriers are in the form of filters and are typically inserted through either the femoral vein (femoral approach) in the patient's leg or the arm or right jugular vein in the patient's neck (jugular approach) under local anesthesia. The filters are then deployed intravascularly in the inferior vena cava where they expand to block migration of the blood clots from the lower portion of the body to the heart and lungs.

Since numerous filters which can be inserted via both the femoral and jugular approaches have a filtering portion downstream of a mounting (anchoring) portion, the surgeon must ensure that the filter is placed in the correct orientation so that the filtering portion is positioned to capture blood clots. Insertion and placement in the wrong orientation would cause the filter to be inoperative and could cause thrombosis. With certain filters, the wrong orientation could result in the anchoring features of the filter failing to grasp the vessel, resulting in migration of the filter to the central venous vasculature which could cause obstruction, vessel perforation, dysrhythmia or even death.

One attempt to orient the filter in the proper position is the cartridge being marketed by Cordis for placement of its Optease* vena cava filter. The cartridge, which contains the filter inside, has arrows labeled jugular or femoral to designate the direction to attach via snap fit the cartridge to the delivery instrument. However, if improper attention is paid by the user to the arrows, the user could easily attach the cartridge to the delivery instrument in the incorrect orientation, causing the problems enumerated above.

B. Braun markets another cartridge for delivery of their Vena Tech* filter. The cartridge has a femoral end colored red and a jugular end colored blue. A corresponding red pusher and blue pusher are provided which can only fit into the respective ends of the cartridge. The selected pusher is intended to be inserted into the cartridge prior to mounting of the cartridge to the delivery instrument However, the surgeon can mistakenly mount the cartridge in the wrong orientation by threading the cartridge first onto the delivery system (in the wrong orientation), and then inserting the pusher.

In U.S. Pat. No. 6,328,755, a filter cartridge is disclosed with a hinged locking mechanism. Orientation of the cartridge is not addressed.

In commonly assigned co-pending patent application Ser. No. 10/889,429, filed Jul. 12, 2004, a cartridge is disclosed with a pair of locking rails engaged by a detent to hold the cartridge in place. Markings on the cartridge indicate the jugular or femoral orientation. However, this cartridge suffers from the disadvantages enumerated above since the surgeon must rely solely on the markings for cartridge orientation.

It would be advantageous to provide a filter cartridge which is easily mounted to a delivery system component and which reduces the chances of being loaded in the incorrect orientation. Such cartridge could advantageously be used to load various types of filters. Other vascular devices also require correct orientation within the vessel. Therefore, it would be advantageous to provide a cartridge which could load various vascular devices and mount to a delivery system for the vascular device.

SUMMARY

The present invention overcomes the problems and deficiencies of the prior art. The present invention provides a cartridge for holding a vascular device and connectable to a component of a delivery system. The cartridge comprises a housing having an engagement member movable to a first engageable to engage the component of the delivery system to connect the cartridge to the component in a first orientation. A control member is operatively associated with the engagement member to move the engagement member to the first engageable position.

In one embodiment, the cartridge includes a second engagement member movable to a second engageable position to engage the component of the delivery system. Preferably, the first engagement member is movable in a first direction to the first engageable position to connect the cartridge in a first orientation and the second engagement member is movable in a second direction to a second engageable position to connect the cartridge in a second orientation. In a preferred embodiment, the engagement members have snap-fit features exposed in the first engageable position to snap fit with the component of the delivery system.

In a preferred embodiment, the non-engageable position corresponds to a retracted position of the engagement member and the engageable position corresponds to an extended position of the engagement member.

In a preferred embodiment, the first and second engagement members are on opposing end portions of a sliding member.

The control member preferably comprises a post movable (e.g. slidable) within an opening in the housing, with the opening preferably including retention structure (e.g. a detent) to retain the post in a neutral position corresponding to a first non-engageable position of the engagement member. In one embodiment, the opening has an axial component and a radial component wherein the post is positioned in the radial component to retain the engagement member in the extended position.

The cartridge may further include indicia on the housing to indicate the femoral and jugular orientations.

The present invention further provides a method of connecting a vascular device to a component of a delivery system for delivering the vascular device to a patient, the method comprising:

providing a cartridge dimensioned to contain a vascular device;

determining whether a first approach or a second approach for device insertion is desired;

orienting the cartridge to correspond to the approach determined; and moving an engagement member to a connection position for connection of the cartridge to a component of the delivery system.

In a preferred embodiment, the step of moving the engagement member preferably comprises the step of moving a control member extending from the cartridge to move the engagement member from a retracted position within the cartridge. The cartridge can contain indicia to indicate a first, e.g. femoral, and a second, e.g. jugular, orientation of the cartridge, and the step of moving the control member preferably comprises moving the engagement member in the direction indicated by the indicia.

BRIEF DESCRIPTION OF THE DRAWINGS

Preferred embodiment(s) of the present disclosure are described herein with reference to the drawings wherein:

FIG. 1 is a perspective view of the cartridge of the present invention;

FIG. 2 is a longitudinal cross-sectional view taken along line 2-2 of FIG. 1 showing the cartridge containing a vessel filter;

FIG. 3 is an exploded view of the cartridge;

FIG. 4 is a perspective view of the cartridge illustrating the knob being moved from its neutral position in a first direction to expose the engagement member for a femoral delivery approach;

FIG. 5 is a broken perspective view of the introducer sheath and pusher of the delivery system and a perspective view of the cartridge prior to connection to the hub of the sheath wherein the cartridge is shown with the knob in the first extended position to fully expose the engagement member for femoral orientation and connection;

FIG. 6 is a perspective view showing the cartridge of FIG. 5 attached to the hub of the introducer sheath of the delivery system;

FIG. 8A illustrates delivery of the filter via a femoral approach;

FIG. 8B illustrates placement of the filter in the inferior vena cava;

FIG. 9 is a longitudinal cross-sectional view similar to FIG. 7 except showing the knob moved in a second direction to a second extended position to expose the engagement member from an opposing side of the cartridge for a jugular delivery approach;

FIGS. 10A and 10B illustrate perspective views of the cartridge showing the position of the knob and engagement member for the jugular approach;

FIG. 11A illustrates delivery of the filter via the jugular approach;

FIG. 11B illustrates placement of the filter in the inferior vena cava;

FIG. 12A is a perspective view of one vascular device (a filter) which can be inserted using the cartridge of the present invention;

FIG. 12B is a perspective view of the filter of FIG. 12A shown in the collapsed position;

FIG. 12C is a close-up side view of the retention hooks of the filter of FIG. 12B; and FIGS. 13 and 14 are perspective views of other vascular devices which can be inserted using the cartridge of the present invention.

DETAILED DESCRIPTION OF PREFERRED EMBODIMENTS

Figure 7:
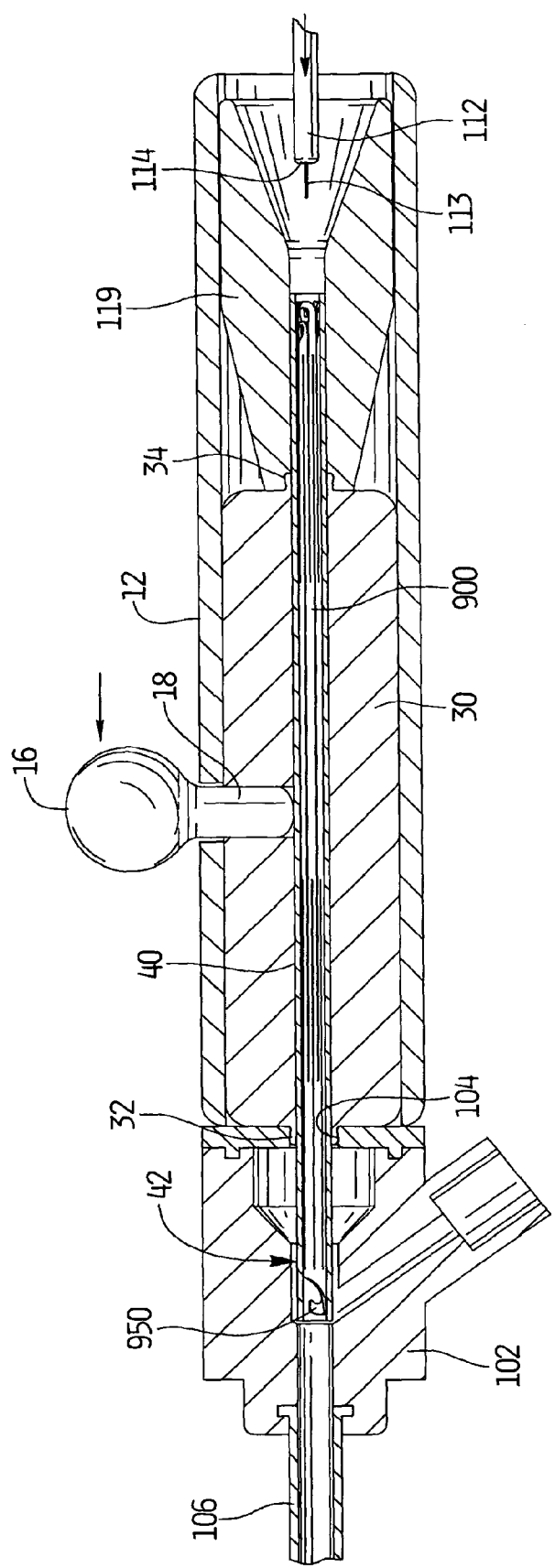
FIG. 7 is a longitudinal cross-sectional view taken along line 7-7 of FIG. 6.

Turning now to the drawings, wherein like reference numerals identify similar or like components throughout the several views, a delivery system for delivery and placement of a vascular device is disclosed. The system includes a cartridge containing the vascular device which is mounted to a component of the delivery system. Various vascular devices can be contained within the cartridge such as a filter, an aortic valve, replacement valves, etc. By way of example, a vascular filter will be described and shown throughout the drawings as the vascular device contained in the cartridge, it being understood that other devices can alternatively be contained in the cartridge.

Since the surgeon can deliver the filter to the vessel using either a femoral approach (through the femoral vein in the leg) or a jugular approach (through the jugular vein in the neck), the cartridge of the present invention is designed to facilitate the correct orientation of the cartridge so that the filter is delivered to the vessel in the correct orientation. This is achieved not only through the provision of visual indicators on the cartridge but by a sliding mechanism in the cartridge which needs to be moved by the user in order to mount the cartridge to the delivery system component.

Turning now to the details of the cartridge of the invention, with reference to FIGS. 1-4, cartridge 10 has a housing 12, a slide 30 slidably received within housing 12, a tube 40 and a knob 16. Formed within housing 12 is an opening 20, preferably in the form of a slot, which has a longitudinal component 22, a first radial component 24 and a second radial component 26. Post 18 of knob 16 slides within slot 20 as described in more detail below. A filter 900, corresponding to the filter of FIG. 12, is shown within tube 40 by way of example. As will become apparent from the discussion below, other filters as well as other vascular devices can be contained in the cartridge 10.

Slide 30 contains an aperture 39 to receive post 18 of knob 16. Post 18 of knob 16 extends slightly into the interior of slide 30 and is rigidly affixed thereto so that the knob 16 can be grasped by the user and moved within slot 20 to thereby move the slide 30 within the housing 12. In an alternate embodiment, the knob 16 is snap-fit into the aperture 39.

Slide 30 includes a first engagement member 32 at one end and a second engagement member 34 at the opposite end, each of which provides a snap fit feature. In the initial neutral position of FIGS. 1 and 2, slide 30 is positioned within housing 10 such that both the first and second engagement members 32, 34 are contained substantially within the housing 10.

In this position, both engagement members 32, 34 are in their non-engageable position which corresponds to a retracted position in the illustrated embodiment. When knob 16 is moved in one direction, e.g., the direction of the arrow for a femoral approach, the slide 30 is moved in the same direction to advance the first engagement member 32 from a first non-engageable, e.g. retracted, position in the housing 12 to a first engageable, e.g. extended, position so the first snap fit feature is exposed. When the knob 16 is moved in the opposite or second direction, e.g., the direction of the arrow for jugular approach, the slide 30 is moved in this second direction to advance the second engagement member 34 from the first non-engageable, e.g. retracted, position in the housing 12 to a second engageable, e.g. extended, position so the second snap fit feature is exposed. The radial components of the slot 20 function to retain the knob 16 and post 18 in the first or second extended position. Furthermore, detent 25 (see FIG. 4) helps maintain the knob 16 in the neutral position (corresponding to the retracted position of the engagement members) by requiring overriding a predetermined force to move the knob. Other retention structure for the knob 16 is also contemplated such as a tapered region.

The vessel filter is contained in tube 40. This tube 40 is positioned in the longitudinal opening extending through slide 30 and is fixedly secured within slide 30 by adhesive so it moves as the slide 30 moves. In an alternate embodiment, slide 30 is insert molded over tube 40. When slide 30 is moved in a femoral direction by knob 16, the first end portion 42 of tube 40 is extended from a first end of housing 12 (see e.g., FIG. 7). When slide 30 is moved in the opposite jugular direction, second end portion 44 is extended from a second end of housing 12 (see e.g., FIGS. 9 and 10). The extended tube portions 42, 44 also provide a guide for cartridge connection as they extend into the hub opening (described below). A pusher of the delivery system, described below, engages the filter to advance it from the tube 40 along the delivery tube of the delivery system for deployment into the vessel.

With reference to FIGS. 5-7, the cartridge 10 is mounted to the hub component 102 of the introducer sheath 101 of the delivery system. The pusher component of the delivery system is designated by reference numeral 110. The pusher 110 has a pusher tube 112 and a wire 113 which can be made of Nitinol, extending from the pusher tube 112. The wire extends through the cartridge 10 and through the length of delivery tube 106 of introducer sheath 101 to maintain a separation of the retention hooks of the filter during insertion of the delivery system and delivery of the filter through tube 106. A conical tube 119 is placed over the free end of tube 40 and snap fitted onto the free engagement member, i.e., the engagement member which is not engaged with the hub, to provide a lead in for the wire 114. As shown, the snap-fit engagement of the snap fit feature of the engagement member 32 (or 34) of the cartridge 10 within wall 104 of opening 105 of proximal cap 109 connects the cartridge 10 to the delivery system, i.e. the introducer sheath 101. Other modes of attachment are also contemplated. Markings "jugular" and "femoral" on the outer surface of the housing 12 indicate a femoral or jugular direction so the user knows the orientation to attach the cartridge 10 to hub 102, i.e., whether snap-fit feature of engagement member 32 or 34 should be exposed and engaged. FIG. 7 illustrates snap-fit feature of engagement member 32 engaged with hub 102 for providing femoral insertion; FIG. 9 illustrates snap-fit feature of engagement member 34 engaged with hub 102 for providing jugular insertion. As shown, in FIG. 7 knob 16 has been moved from its neutral position to its femoral position; in FIG. 9 knob 16 has been moved from its neutral position to its jugular position.

Once the cartridge 10 is attached, advancement of the pusher 110 advances pusher tube (or rod) 112 to advance the filter from the cartridge 10 and through tube 106 as the distal edge 114 of the pusher tube 112 abuts the proximal end of the filter, with the wire 113 preventing entanglement of the retention hooks. The wire 113 also provides support (stability) for the pusher 110 as the pusher 110 is advanced over the wire. Once the filter is positioned adjacent the opening 108 of delivery tube 106, the introducer sheath 101 is retracted to release the filter through the distal end opening 108 of the tube 106. A visual indicator, e.g. a ring (not shown), could be provided on the pusher tube 112 to indicate when the filter is adjacent the opening 108 so the user knows not to advance the pusher tube 112 further. Port 107 in hub 102 provides an inlet for attachment of a tube for infusion of cold saline as described in more detail below.

Various filters can be utilized with the cartridge of the present invention. These filters are designed for placement within the inferior vena cava to capture blood clots or other particles which could otherwise pass to the lungs. The filters are movable from a low profile collapsed configuration to facilitate insertion through the delivery sheath to a larger expanded placement configuration to engage the vessel walls to secure (mount) the filter within the inferior vena cava.

One example of a filter which can be inserted using the cartridge of the present invention is illustrated in FIGS. 12A-12C. This filter is described in detail in pending U.S. patent application Ser. No. 10/889,429, filed Jul. 12, 2004, the entire contents of which are incorporated herein by reference. In this bell shaped filter 900, the elongated struts have a first angled region of interconnecting (connecting) struts 914a, 914b in the filtering region 919 and a second angled region of interconnecting (connecting) struts 914e, 914f in the mounting region 921 of greater transverse dimension. That is, connecting strut portion 914a of one strut 914 interconnects with the connecting strut portion 914b of an adjacent strut at joining region 914d. This forms closed geometric shapes 925. After convergence of strut portions 914a, 914b at joining region 914d, it transitions into elongated mounting strut portions 914c which form flared mounting or anchoring region 921. Strut portions 914e, 914f form connecting portions to connect adjacent strut portions 914c as connecting strut 914e of one strut is connected to connecting strut 914f of an adjacent strut. Connecting strut portion 914e on one strut and portion 914f of another strut converge at end (joining) region 929, as closed geometric shapes 935 are formed.

The filtering region 919 converges at portion 932 into tubular portion 918. The tubular portion 918 is preferably in the form of a retrieval hook 950 as described in the '429 application which has a cut out to expose an annular interior surface to accommodate a portion of a tubular snare sheath.

Strut portions 914c terminate in hooks 940a, 940b which lie in the plane of strut 914. Hooks 940a are larger than hooks 940b and smaller hooks 940b nest within larger hooks and are spaced axially (inwardly) of hooks 940a as well as spaced axially with respect to each other.

Filter 900 is preferably manufactured from a cut laser tube of shape memory material, such as Nitinol, a nickel titanium alloy, or elgiloy. The collapsed configuration of the filter reduces the overall profile to facilitate delivery to the site. The diameter or transverse dimension of the filter in the collapsed configuration is preferably about 2 mm and more preferably about 1.7 mm. The diameter or transverse dimensions of the filter in the expanded configuration could range from about 18 mm to about 32 mm, depending on the internal diameter of the vessel. To facilitate passage of the filter 900 through the lumen of the delivery tube 106, cold saline is injected into the delivery tube 106 (or catheter) around the filter in its collapsed position. The cold saline maintains the temperature dependent filter in a relatively softer condition as it is in the martensitic state within tube 106. This facilitates the exit of the filter from the tube as frictional contact between the filter 10 and the inner surface of the tube would otherwise occur if the filter was maintained in a rigid, i.e. austenitic, condition. Once ejected from tube 106, the filter is no longer cooled and is exposed to the warmer body temperature, which causes the filter 900 to return towards its austenitic memorized configuration.

FIGS. 8A and 8B illustrate delivery of the filter 900, by way of example, in the inferior vena cava "v" via a femoral approach. Once a femoral approach is decided, the knob 16 of the cartridge 10 is slid in the direction of the femoral arrow to expose the snap fit feature of engagement member 32 (see FIG. 7). It is rotated into the radial slot component 24 to maintain it in place. The cartridge 10 can then be snap fitted onto the hub 102 of introducer sheath 101. (Note the cartridge cannot be snap fitted onto the hub with the knob 16 in the neutral position because the snap fit feature is not sufficiently exposed.) The delivery system is inserted into the femoral vein "f" and advanced through the iliac arteries into the inferior vena cava "v". Extension 107 of hub 102 receives tubing 350 to enable saline injection. The pusher 110 is advanced so filter 900 is advanced from cartridge 10 by pusher tube 114 and through tubing 106 of sheath 101, to a position adjacent tube opening 108. The introducer sheath is then withdrawn so the filter exits through opening 108 exposing the filter to enable filter it to be warmed by body temperature to transition to the expanded placement configuration. Note it is implanted in the orientation such that filter section 919 is downstream of the flared anchoring section 921 as shown in FIG. 8B. This enables blood clots or other particles to be directed to the center of the filter section by the angled struts. Thus, correct orientation of filter placement can be appreciated.

FIG. 11 illustrates insertion of filter 900, by way of example, through the internal jugular vein into the inferior vena cava "v". Once a jugular approach is determined, knob 16 is slid along axial slot 20 in the direction of the jugular arrow to expose the snap fit feature of the engagement member 34 (see e.g., FIGS. 9 and 10). Knob 16 is then rotated into the second radial component 26 to retain the snap feature of an engagement member 34 in the extended (exposed) position. The snap feature is then connected to the hub 102 of the introducer sheath of the delivery system and the pusher tube 114 of pusher 110 advances the filter through tube 106 of sheath 101 as described above to a position adjacent opening 108. Withdrawal of sheath 101 exposes the filter to warmer body temperature where it transitions to the expanded configuration. Note that as implanted, filter section 919 is downstream of flared anchoring section 921.

Note the other filters described herein could be inserted in the same manner as described above via a femoral or jugular approach.

The filter 900 can be removed from access through the internal jugular vein or femoral vein. Various methods can be used to remove the filter such as those described in commonly assigned co-pending application Ser. No. 09/911,097, filed Jul. 23, 2001, now published application 2002-0193827-A1, published Dec. 19, 2001, the entire contents of which is incorporated herein by reference, including, for example, slotted hooks, graspers, etc. For example, the recess or cutout in the tubular end portions of filter 900 receives a snare or other device for removal.

Cold saline is injected during the removal process to cool filter 900 to change the temperature to transition to a softer martensitic state to facilitate removal. That is, injection of cold saline will cause the filter to approach its martensitic state, bringing the filter to a more flexible condition. The flexible condition facilitates the collapse and withdrawal of the filter into the retrieval sheath by decreasing the frictional contact between the filter and the inner surface of the retrieval sheath.

The cartridge of the present invention can also be used for loading other vascular devices which can be delivered through different approaches, e.g. a femoral approach, a jugular approach etc. . . . For example, stent grafts, an aortic valve, a replacement valve with vessel wall approximation features, etc., could be positioned within the cartridge and the cartridge connected to a component of a delivery system in the same manner described above to ensure correct orientation and placement of the vascular device.

FIG. 13 illustrates an example of a vascular device which can be contained within the cartridge of the present invention. The device 400, disclosed in U.S. Pat. No. 6,676,698, the entire contents of which are incorporated herein by reference, has vessel engaging members 451 which approximate the vessel walls and a replacement valve 450. The device would be retained in the cartridge in a collapsed configuration and moved to the expanded configuration as shown in FIG. 13 when placed in the vessel. Other devices of the '698 patent could also be contained within the cartridge of the present invention.

FIG. 14 illustrates an example of another vascular device which can be contained within the cartridge of the present invention. The device 10 disclosed in U.S. Patent Publication No. 2004/0225353, published Nov. 11, 2004 (Ser. No. 10/429,536, filed May 5, 2003), the entire contents of which are incorporated herein by reference, has wire rings 12 and 14, pulled together by tensioning suture 24, and valve leaflets 30. The device would be retained in the cartridge in a collapsed configuration and moved to the expanded configuration of FIG. 14 for vessel placement.

While the above description contains many specifics, those specifics should not be construed as limitations on the scope of the disclosure, but merely as exemplifications of preferred embodiments thereof. For example, the filters can be inserted in other regions of the body in addition to the regions disclosed. Those skilled in the art will envision many other possible variations that are within the scope and spirit of the disclosure as defined by the claims appended hereto.

What is claimed is:

1. A cartridge for holding a vascular device and connectable to a component of a delivery system, the delivery system delivering the vascular device to a patient, the cartridge comprising a housing having a first end and a second end, a vascular device positioned therein, and a first engagement member positioned within the housing and slidable with respect to the housing between a first non-engageable position and a second engageable position for attachment to the delivery system in a first orientation such that the vascular device can be delivered from the cartridge to the delivery system, and a slidable control member including a control knob positioned intermediate the fist and second ends of the housing and extending transversely through the housing and operatively associated with the first engagement member, the control knob movable from a position between the first and second ends toward the first end to slide the first engagement member within the housing between the first non-enageageable position and the second engageable position, and a second engagement member positioned within the housing and movable from a third non-engageable position to a fourth engageable position to engage the component of the delivery system to connect the cartridge to the component in a second orientation such that the vascular device can be delivered from the cartridge to the delivery system.

2. The cartridge of claim 1, wherein the control member is movable in a first direction to slide the first engagement member in the first direction to the first engageable position to connect the cartridge in the first orientation and the control member is slidable in a second different direction to slide the second engagement member in the second different direction to the second engageable position to connect the cartridge in a second orientation.

3. The cartridge of claim 1, wherein the engagement members each have a snap fit feature configured to snap fit with the component of the delivery system in the engageable position.

4. The cartridge of claim 1, wherein the first and second engagement members are on opposing end portions of a sliding member.

5. The cartridge of claim 1, wherein the first and second engagement members are formed on opposing ends of a tube and have a respective opening for the delivery of the vascular device from the tube to a delivery tube.

6. The cartridge of claim 1, wherein the control member comprises a post movable within an opening in the housing.

7. The cartridge of claim 6, wherein the opening includes retention structure to retain the post in a neutral position corresponding to a first non-engageable position of the engagement member.

8. The cartridge of claim 6, wherein the opening has an axial component and a radial component, the post positioned in the radial component to retain the engagement member in the first engageable position.

9. The cartridge of claim 8, further comprising a retention structure to retain the post in at least one of the positions of the engagement member.

10. The cartridge of claim 1, further comprising indicia on the housing to indicate the first and second orientations.

11. The cartridge of claim 1, wherein the vascular device is a graft.

12. The cartridge of claim 1, wherein the vascular device is a replacement valve.

* * * * *